United States Patent

Bzoch

[11] Patent Number: 5,558,628
[45] Date of Patent: Sep. 24, 1996

[54] ADJUSTABLE HIP AND KNEE ORTHOSIS

[75] Inventor: Jan J. Bzoch, South Pasadena, Fla.

[73] Assignee: Orthosis Corrective Systems Corp., Pinellas Park, Fla.

[21] Appl. No.: 447,989

[22] Filed: May 23, 1995

[51] Int. Cl.$^6$ ...................................... A61F 5/00
[52] U.S. Cl. .............................. 602/24; 602/23; 128/882
[58] Field of Search ....................... 602/5, 23–25, 602/33, 35, 40; 128/882

[56] References Cited

U.S. PATENT DOCUMENTS

| | | | |
|---|---|---|---|
| 1,635,638 | 7/1927 | Rogers | 128/882 |
| 1,845,338 | 2/1932 | Querna | 128/882 |
| 2,588,411 | 3/1952 | Robinson | 602/24 |
| 2,630,801 | 3/1953 | Mest et al. | 602/24 |
| 2,906,261 | 9/1959 | Craig | 602/24 |
| 3,892,231 | 7/1975 | Tummillo | 602/24 |
| 4,607,629 | 8/1986 | Lerman | 602/24 |
| 5,311,366 | 5/1994 | Gerace | 602/24 X |
| 5,362,305 | 11/1994 | Varn | 602/23 X |

FOREIGN PATENT DOCUMENTS

| | | | |
|---|---|---|---|
| 535947 | 11/1976 | U.S.S.R. | 602/24 |
| 741872 | 6/1980 | U.S.S.R. | 602/24 |
| 1147393 | 3/1985 | U.S.S.R. | 602/24 |
| 996562 | 6/1965 | United Kingdom | 602/24 |

OTHER PUBLICATIONS

L'Nard Restorative Concepts, Inc. L'Nard Hip and Knee Abductor 2 pages.
MMAR Medical Group, Inc. M & M Variflex 1 page.
Orthosis Corrective Systems, Inc. Oscar HKO 2 pages.
Restorative Care of America, Inc. RCAI Hip and Knee Abductor 3 pages.
Orthotic Rehab. Products, Inc. Vari-Duct Hip and Knee Orthosis 3 pages.

Primary Examiner—Linda C. Dvorak
Attorney, Agent, or Firm—James E. Larson; Herbert W. Larson

[57] ABSTRACT

A center abduction bar attached at opposite ends to T-shaped connecting elements held in place by thumb screws, the connecting elements attached to side plates conforming to the shape of a patient's thigh and a soft covering over the side plates. The center abduction bar has an inner bar and outer tube to permit adjustment of the center bar's width and to control abduction of the patient's knee and hip. A thumb screw on the abduction bar controls the width setting.

7 Claims, 3 Drawing Sheets

ADJUSTABLE HIP AND KNEE ORTHOSIS

BACKGROUND OF THE INVENTION

1. Field of The Invention

This invention relates to hip and knee orthosis devices. More particularly, it relates to a hip and knee abductor having an adjustable center bar.

2. Description of Prior Art

Hip and knee orthosis devices are known in the prior art. They are used to stabilize the hip and knees of a patient who has experienced trauma to the lower portion of the body. The prior art hip and knee orthosis devices have a pair of rigid members for positioning juxtaposed to the inner thigh portion of the patient. A soft and pliable material is inserted over the rigid members for contact with the person's skin. A center element is mounted between the rigid members retaining the patient's hip and knees in a stabilized position for treating hip and knee contractures and post operative lower extremity abduction.

Recent improvements in the center element have enabled the orthosis to be adjusted permitting hip and knee abduction and range of motion to the affected joints. The improvements provided a center bar having a plurality of holes for receiving a spring loaded pin. The pin can be positioned in any one of the holes for providing different levels of abduction. Although the device has proven to be effective in providing different levels of abduction, the repositioning of the pin has proven to be awkward. For this reason, an improved hip and knee orthosis having an adjustable center element able to provide different settings of abduction in a fast and easy manner is desired.

SUMMARY OF THE INVENTION

I have developed an improved hip and knee orthosis for fast and easy use.

The orthosis has a center abduction bar with T-shaped connecting elements attached on each end. The connecting elements are in turn attached to a convex surface of a curved plate with its opposite concave surface conforming to the thigh of a patient. The curved plates are covered with a soft fabric that is wrapped around the thigh of a patient and attached with hook and loop material.

The abduction bar has an outer tube and inner bar slidable within the outer tube. Threaded bores at each end of the abduction bar permit adjustment of the T-shaped connecting element by use of a thumb screw. A slot in the outer tube permits adjustment of the width of the abduction bar by fastening a thumb screw to a threaded bore in the inner bar through the slot.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
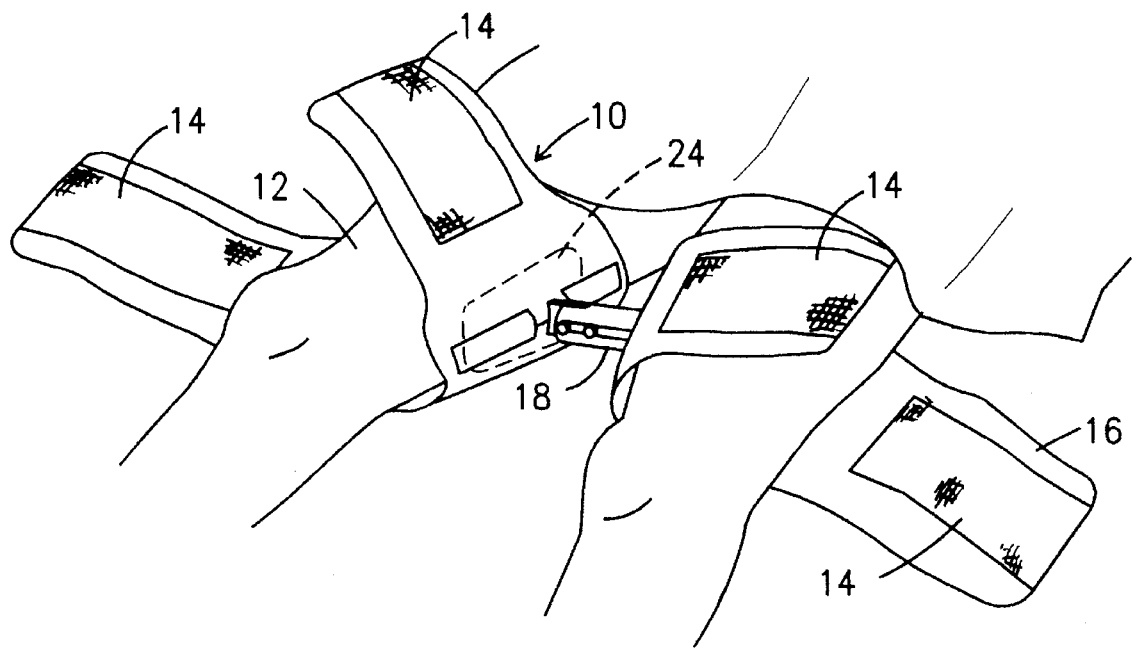
FIG. 1 is a perspective view of the hip and knee abductor of the present invention being applied onto a patient.
Figure 2:
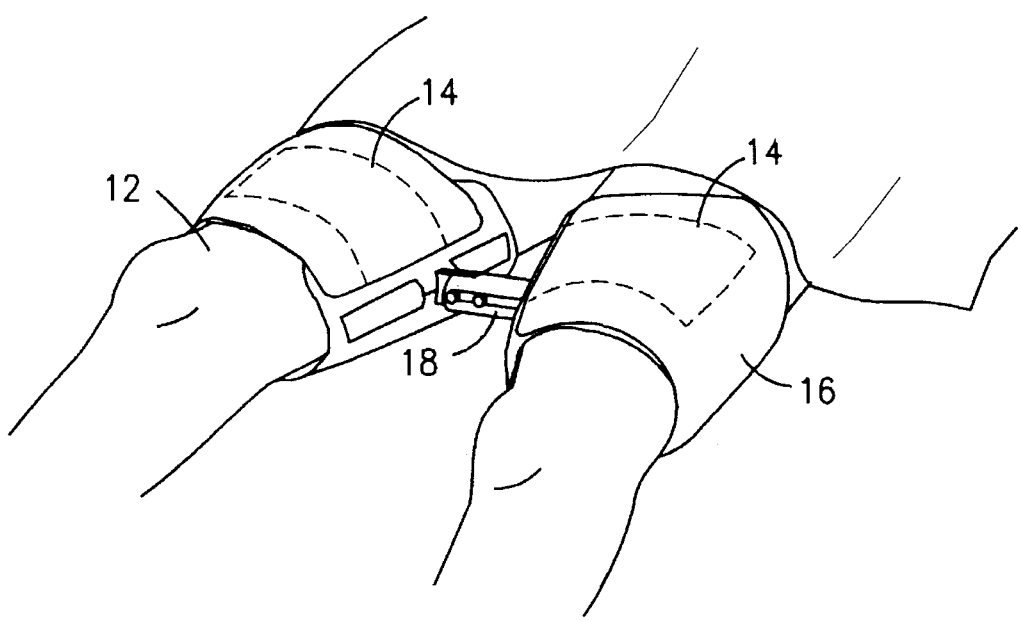
FIG. 2 is a perspective view of the hip and knee abductor fully applied to the patient.
Figure 3:
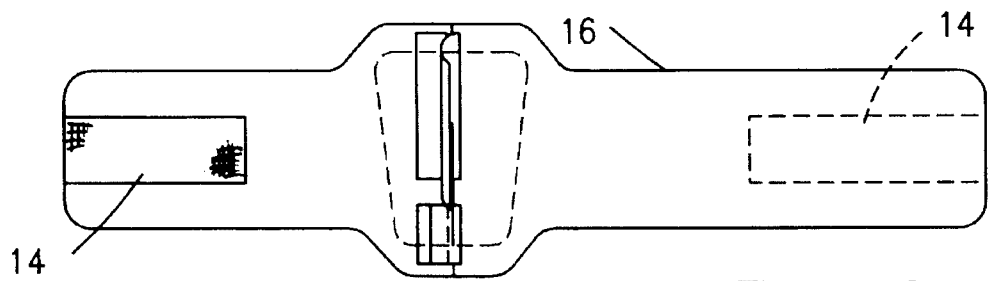
FIG. 3 is a side elevational view of the hip and knee abductor of the present invention showing an outer surface of the leg securing member.
Figure 4:
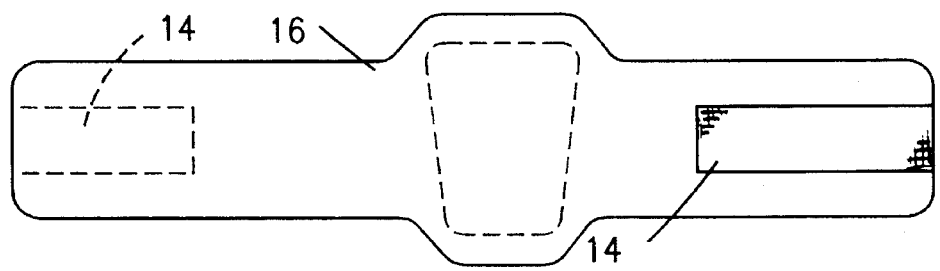
FIG. 4 is a side elevational view of the hip and knee abductor showing an inner surface of the leg securing member.

Referring to FIG. 1, the hip and knee orthosis 10 is wrapped around the thighs 12 of a patient for the purpose of spreading the hip and knee of a patient within a range of 30° to 40°.

Hook and loop material 14 sewn into soft fabric 16 is used to bind the orthosis 10 to the thigh 12 on the patient. Abduction is created by an abductor bar 18 having a first T-shaped connecting element 20 attached at a first end 17 and a second T-shaped connecting element 22 attached at a second end 19. The first T-shaped connecting element 20 is attached to an outer convex surface 23 of a first curved plate 24. The second T-shaped connecting element is attached to an outer convex surface 25 of a second curved plate 26. The inner surface of both plates 24 and 26 are concave and conform to the shape of the patient's thigh 12.

The abductor bar 18 has an inner bar 27 containing a first threaded bore 28 and an outer tube 29 with a second threaded bore 30. In addition, the outer tube 29 has a slot 32 with multiple thumb screw mounting positions 34. A third bore 36 in the inner bar is aligned with the slot 32 in the outer tube.

A first thumb screw 38 is screwed into the first threaded bore 28. A second thumb screw 40 is screwed into the second bore 30 and a third thumb screw 42 is screwed into the third bore 36. When thumb screw 38 is unscrewed from bore 28, it allows the first T-shaped connecting element 20 to move since tongue 52 is no longer fixed in position within slot 58 in the inner bar 27. In like manner, thumb screw 40 releases tongue 54 to move within slot 60 of outer tube 29. A plastic liner 56 prevents wear on the tongues 52 and 54, respectively. Set screws 50 prevents the first or second T-shaped element 20 or 22 from detachment from the abductor bar 18.

Figure 7:
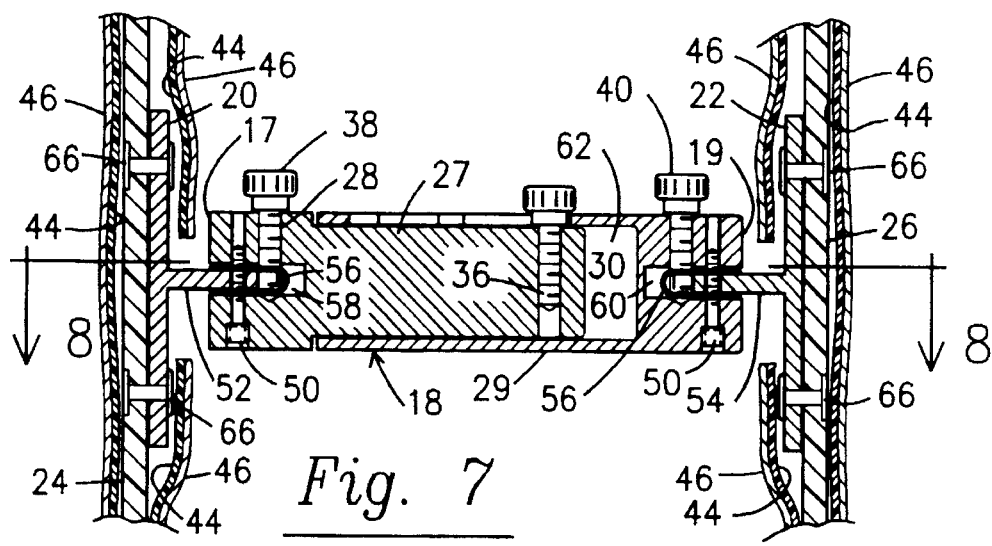
FIG. 7 is a cross-sectional view of the hip and knee abductor along lines 7—7 of FIG. 5.
Figure 8:
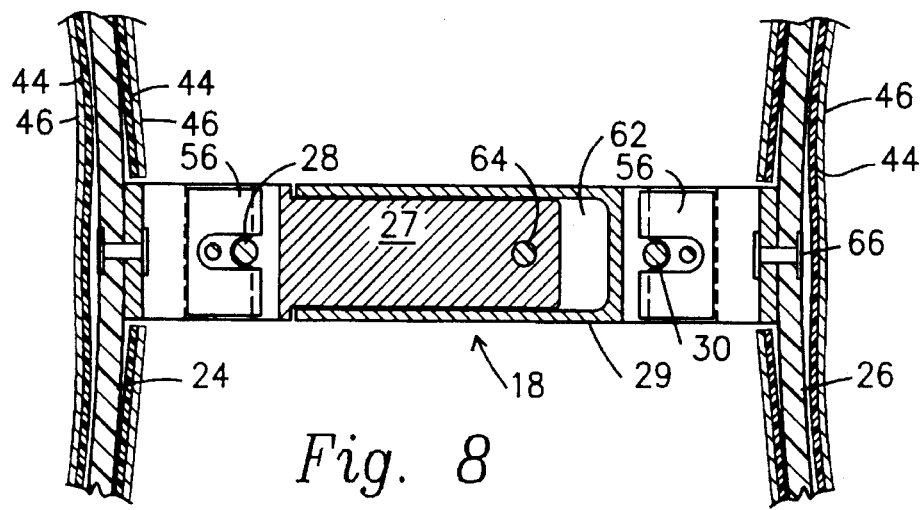
FIG. 8 is a cross-sectional view of the hip and knee abductor along lines 8—8 of FIG. 7.
Figure 9:
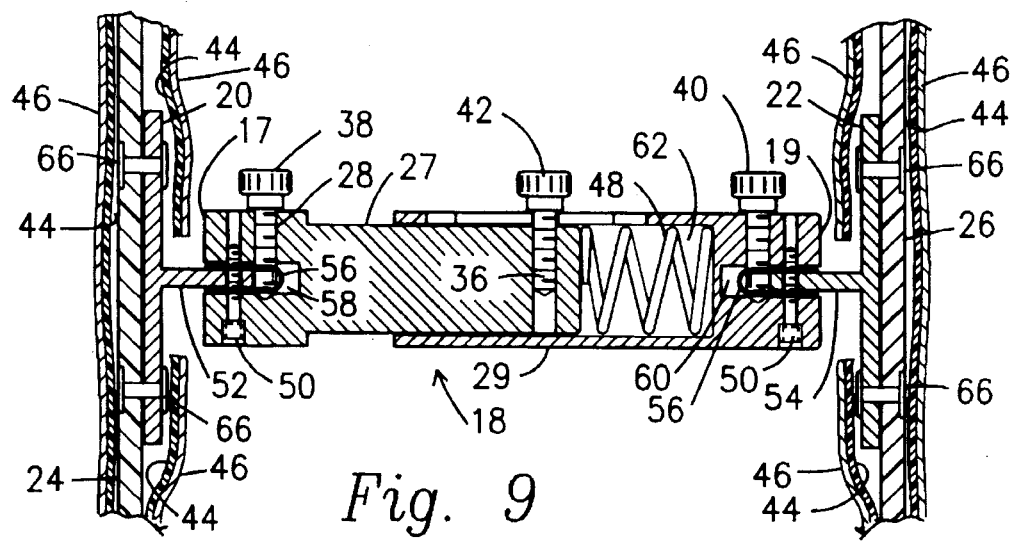
FIG. 9 is a cross-sectional view of the hip and knee abductor along lines 7—7 of FIG. 5 with a spring member added.

As seen in FIGS. 7–9, the soft fabric 16 has an inner foam layer 44 and on each side of the foam 44 there is a thin layer of soft fabric 46.

Optionally, as seen in FIG. 9, a resilient member or spring 48 can be located within inner chamber 62 of the outer tube 29 so that bar 27 is urged away from chamber 62.

Figure 5:
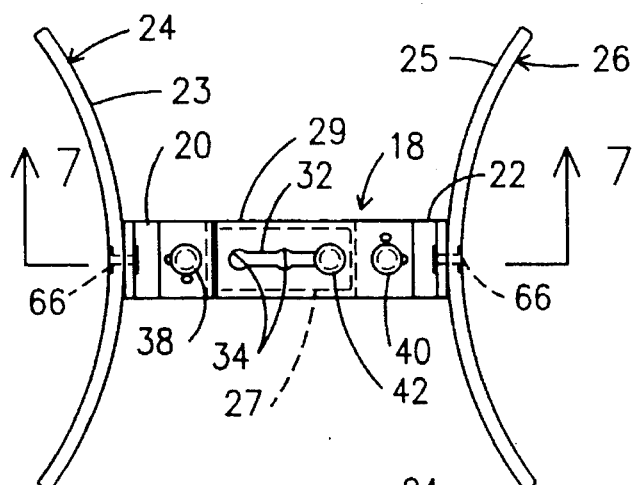
FIG. 5 is a top plan view of the hip and knee abductor of the present invention showing a telescopic inner bar in its fully closed position.
Figure 6:
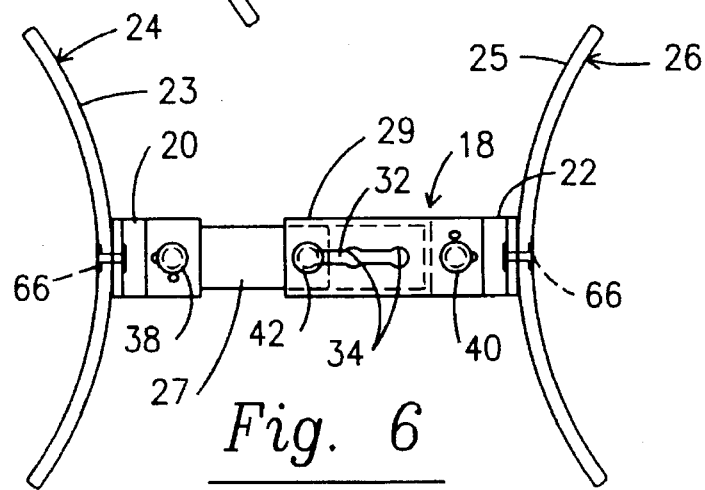
FIG. 6 is a top plan view of the spreader apparatus showing the telescopic inner bar in its fully extended position.

Removal of thumb screws 38 and 40 permit ambulation of the patient up to about 80°. Withdrawal of the thumb screw 42 allows positioning of the inner bar 27 either at its furthest point, FIG. 6, or nearest point, FIG. 5, with respect to outer tube 29. Thumb screw slot positions 34 are shown in FIG. 5 and FIG. 6. FIG. 5 shows the thumb screw 42 inserted closest to the second T-shaped connecting element 22 and FIG. 6 shows the extended position where thumb screw 42 is closer to the first T-shaped connecting element 20.

The abductor 18 can be made of extruded aluminum, stainless steel or a high strength polymer. The soft fabric 46 can be a type of liner material called "headliner" and the inner foam 44 can be a foam material sold by EASTMAN KODAK COMPANY under the trademark "KODEL". The first and second curved plates 24 and 26, respectively can be made from a hard polymer, aluminum or stainless steel. The T-shaped connecting elements 20 and 22 can be attached to plates 24 and 26 by bolts 66 or rivets. A set screw 64 can be inserted in a bore within the inner bar 27 aligned with a bore in the outer tube 29 in order to permanently affix the abductor bar in a closed position.

Through the use of this improved hip and knee orthosis, patients can easily adjust the orthosis for ambulation without removing it completely from their thighs and patient care personnel can change the position of the abduction merely by moving thumb screw 42 into a different position within slot 32.

Equivalent elements can be substituted for the ones set forth above to achieve the same results in the same manner.

Having thus described the invention what is claimed and desired to be secured by Letters Patent is:

1. A hip and knee orthosis for attaching to opposed distal thighs of a patient comprising a center abduction bar, a first and second T-shaped connecting element movably attached at opposite ends of the center abduction bar, the T-shaped connecting elements each attached to a convex surface of a first and second curved plate, an opposite side concave surface of the first and second curved plates shaped to conform substantially to a distal thigh of the patient, the first and second curved plates covered by a soft fabric configured to wrap around the opposed distal thighs of the patient and held together by hook and loop material, the center abduction bar having a first and second threaded bore adjacent a first and second end respectively, a hand operable first and second threaded thumb screw mounted within the first and second threaded bore to maintain the first and second T-shaped connecting elements respectfully in a desired position, the center abduction bar having an inner bar slidable within an outer tube, the inner bar having a third threaded bore adjacent an end distal from the first threaded bore, the outer tube having a multiple position slotted opening extending from a location proximal to the second threaded bore to a location proximal to an end of the outer tube distal from the second threaded bore, a third hand operated threaded thumbscrew mounted within the third threaded bore so that unscrewing of the third threaded screw will allow the inner bar to slide within the outer tube to provide extension or contraction of the orthosis and wherein unscrewing of the first or second thumb screw provides for ambulation of the patient.

2. The hip and knee orthosis according to claim 1 wherein there are three screw fastening positions within the slotted opening on the outer tube.

3. The hip and knee orthosis according to claim 1 wherein the soft fabric covering the first and second curved plates has a foam inner layer covered by soft fabric outer layers.

4. The hip and knee orthosis according to claim 3 wherein the first and second curved plates are made from a hard plastic.

5. The hip and knee orthosis according to claim 1 wherein movement of the inner bar with respect to the outer tube can change the position of abduction for the patient between 30° to 40°.

6. The hip and knee orthosis according to claim 1 wherein release of the first and second thumb screw permits up to 80° range of motion for patient ambulation.

7. The hip and knee orthosis according to claim 1 wherein a resilient member is mounted within the outer tube to resist movement of the inner bar towards the second bore.

* * * * *